United States Patent [19]

Visscher et al.

[11] Patent Number: 5,154,849

[45] Date of Patent: Oct. 13, 1992

[54] MILD SKIN CLEANSING TOILET BAR WITH SILICONE SKIN MILDNESS/MOISTURIZING AID

[75] Inventors: Martha O. Visscher; Theresa A. Bakken, both of Cincinanti; Lawrence A. Gilbert, West Chester; Norman G. Howell, Loveland; Debra D. Watson, Cincinnati, all of Ohio

[73] Assignee: The Procter & Gamble Company, Cincinnati, Ohio

[21] Appl. No.: 614,662

[22] Filed: Nov. 16, 1990

[51] Int. Cl.$^5$ .......................... C11D 8/37; C11D 9/36
[52] U.S. Cl. ................... 252/174.15; 252/117; 252/134; 252/174.23; 252/DIG. 5; 252/DIG. 16
[58] Field of Search .................. 252/174.15, DIG. 16, 252/174.23, 134, 117, DIG. 5

[56] References Cited

U.S. PATENT DOCUMENTS

| | | | |
|---|---|---|---|
| 2,826,551 | 3/1958 | Geen | 252/89 |
| 3,836,647 | 9/1974 | Lange | 424/184 |
| 3,867,549 | 2/1975 | Costello et al. | 424/361 |
| 3,964,500 | 6/1976 | Drakoff | 132/7 |
| 4,234,464 | 11/1980 | Morshauser | 252/544 |
| 4,279,765 | 7/1981 | Hill et al. | 252/117 |
| 4,311,695 | 1/1982 | Starch | 424/184 |
| 4,364,837 | 12/1982 | Pader | 424/70 |
| 4,370,319 | 6/1983 | Chapin et al. | 424/184 |
| 4,478,853 | 10/1984 | Chausse | 424/358 |
| 4,704,272 | 11/1987 | Oh et al. | 424/70 |
| 4,728,457 | 3/1988 | Fieler et al. | 252/174.15 |
| 4,741,855 | 5/1988 | Grote et al. | 252/142 |
| 4,788,001 | 11/1988 | Narula | 252/312 |
| 4,788,006 | 11/1988 | Bolich, Jr. et al. | 252/550 |
| 4,812,253 | 3/1989 | Small et al. | 252/132 |
| 4,842,850 | 6/1989 | Vu | 424/70 |
| 4,879,114 | 11/1989 | Catsimpoolas | 424/95 |
| 4,885,109 | 12/1989 | Umemato et al. | 252/174.21 |
| 4,902,499 | 2/1990 | Bolich, Jr. et al. | 424/70 |
| 4,906,459 | 3/1990 | Cobb et al. | 424/70 |

FOREIGN PATENT DOCUMENTS

| | | |
|---|---|---|
| 1005763 | 2/1977 | Canada . |
| 2019264 | 7/1986 | Canada . |
| 195511 | 5/1982 | Czechoslovakia . |
| 308189 | 3/1989 | European Pat. Off. . |
| 308190 | 3/1989 | European Pat. Off. . |
| 336803 | 10/1989 | European Pat. Off. . |
| 363252 | 4/1990 | European Pat. Off. . |
| 76293 | 9/1970 | German Democratic Rep. . |
| 61-157598A | 7/1986 | Japan . |
| 61-195200A | 8/1986 | Japan . |
| 62-244431 | 10/1987 | Japan . |
| 87309395 | 6/1989 | Japan . |
| 1447254 | 8/1976 | United Kingdom . |
| 2041964 | 9/1980 | United Kingdom . |

Primary Examiner—Paul Lieberman
Assistant Examiner—E. Higgins
Attorney, Agent, or Firm—Robert B. Aylor; Leonard Williamson; Steven J. Goldstein

[57] ABSTRACT

A mild skin cleansing composition in the form of a bar comprising from about 0.5% to about 20% of a mixture of a silicone gum and a silicone fluid wherein the gum:fluid ratio is from about 10:1 to about 1:10, preferably from about 4:1 to about 1:4, most preferably from about 3:2 to about 2:3. The silicone component is a skin mildness/moisturizing aid which imparts superior, durable conditioning to skin washed with the composition. Processes for preparing a mild skin cleansing toilet bar with this silicone component are disclosed.

33 Claims, No Drawings

MILD SKIN CLEANSING TOILET BAR WITH SILICONE SKIN MILDNESS/MOISTURIZING AID

TECHNICAL FIELD

This invention relates to mild skin cleansing toilet bar compositions. More particularly, it relates to mild skin cleansing toilet bars comprising a silicone skin mildness/moisturizing aid component.

BACKGROUND OF THE INVENTION

The cleansing of skin with surface-active cleansing preparations has become a focus of great interest. Many people wash and scrub their skin with various surface-active preparation several times a day. Ideal skin cleansers should cleanse the skin gently, causing little or no irritation, without defatting and overdrying the skin r leaving it taut and rough after frequent routine use. Most lathering soaps and synthetics, liquids and bars included, fail in this respect.

Soaps have for many years been employed as cleansing agents for the skin. Soaps are not mild to the skin, thus the incorporation of additives to improve the performance of soap is a common practice. Superfatting agents, such as lanolin, fatty acid derivatives and lecithin, are often added to mitigate the degreasing effect of the soap on skin. The ability of superfatting agents to produce a soft skin feel is of limited duration.

Certain synthetic surfactants are known to be particularly mild. However, a major drawback of most mild synthetic surfactant systems when formulated for skin cleansing is poor lather performance, when compared to the highest bar soap standards (bars which are rich in coconut soap and superfatted). On the other side, the use of known high sudsing anionic surfactants with lather boosters can yield acceptable lather volume. Unfortunately, the highest sudsing anionic surfactants are, in fact, poor in clinical skin mildness. Surfactants that are among the mildest, such as alkyl (sodium lauryl) glyceryl ether sulfonate (AGS), are marginal in lather. It will be appreciated that these two factors, lather and skin mildness, make the surfactant selection a delicate balancing act.

It is known that moisturizers can provide skin conditioning benefits in cleansing products. For example, glycerin and/or free fatty acids are added to bars or liquid cleansing products for skin benefits. Likewise, certain polymeric skin feel aids can also provide unique tactile characteristics to both the lather and the skin during rinsing. Unfortunately, conventional moisturizers/emollients and polymeric skin feel aids provide a softening effect on human skin while leaving the skin feeling greasy, sticky or tacky.

Silicones have been disclosed for several used in toilet bars. It has been disclosed in Czechoslovakian Patent 195511, List et al., issued May 15, 1982, to incorporate dimethylsiloxane into toilet and shaving soaps to prevent bloom, to decrease bar drying and cracking, and to increase soap homogeneity and plasticity. U.K. Patent Application 2,041,964, Cooper, published Sep. 17, 1980, has disclosed the use of silicone compounds as fragrance-imparting components in bar soaps. Polysiloxane fluids have been taught in East German Patent Application 76293, Limbach et al., published Sep. 20, 1970, to provide a protective film to the skin, to better fixate the perfume and to prevent surface softening of soap bars after contact with water. U.S. Pat. No. 4,279,765, Hill et al., issued Jul. 21, 1981, has disclosed the use of amine-substituted polydiorganosiloxanes to impart a durable soft, silky feel to the skin contacted with the soap bar.

It has now been discovered that mild skin cleansing toilet bar compositions which comprise from about 0.5% to about 20% of a silicone component, consisting of a mixture of silicone gum and silicone fluid, provide durable skin conditioning, superior smooth and soft skin feel, lather and improved rinsing. The use of toilet bar compositions which contain a silicone gum and fluid blend component provides superior skin conditioning without negative tactile attributes such as greasy, sticky or tacky skin feel. Unexpectedly, toilet bar compositions with a silicone gum and fluid blend component provide reduced skin tautness after washing. The skin feel and conditioning imparted by the silicone gum and fluid blend is superior to that provided by the use of silicone fluid alone. In addition, the silicone gum/fluid blends are easier to process in the mild skin cleansing toilet bars of the present invention than the silicone gum alone. Surprisingly, since silicones are known as suds/lather reducers, the silicone gum/fluid blends do not suppress lather in the present invention, even when mild surfactants, which are not known for robust lather, are included.

Silicone gum and fluid blends have been disclosed for use in shampoos and/or conditioners in U.S. Pat. No. 4,906,459, Cobb et al., issued Mar. 6, 1990; U.S. Pat. No. 4,788,006, Bolich, Jr. et al., issued Nov. 29, 1988; U.S. Pat. No. 4,741,855, Grote et al., issued May 3, 1988; U.S. Pat. No. 4,728,457, Fieler et al., issued Mar. 1, 1988; U.S. Pat. No. 4,704,272, Oh et al., issued Nov. 3, 1987; and U.S. Pat. No. 2,826,551, Geen, issued Mar. 11, 1958, all of said patents being incorporated herein by reference. The art does not suggest the use of a silicone gum and fluid blend in a mild skin cleansing toilet bar nor does it suggest that use of such a blend in a mild skin cleansing toilet bar would provide any skin conditioning and moisturizing properties, let alone the superior durable skin conditioning and moisturizing as defined herein, without greasy, sticky, tacky or taut skin feel negatives.

The present invention encompasses a mild skin cleansing toilet bar comprising a specifically defined silicone component which provides improved skin feel, skin conditioning, rinsing and ultra skin mildness without negative tactile attributes, such as greasy, sticky, tacky or taut skin feel.

SUMMARY OF THE INVENTION

The present invention relates to mild skin cleansing composition in the form of bars comprising from about 0.5% to about 20% of a silicone component which consists of the mixture of a silicone gum and silicone fluid wherein the gum:fluid ratio is from about 10:1 to about 1:10, preferably from about 4:1 to about 1:4. Preferred compositions additionally contain a cleaning component which is most preferably a mixture of mild synthetic surfactants and soap.

These compositions are made using a process which comprises the steps of mixing the components in a crutcher, drying, amalgamating, milling, plodding and stamping, wherein the silicone component is premixed with at least a portion of the mild synthetic surfactant cleaning component, preferably an acyl sarcosinate, in the absence of soap, and is then added to the crutcher and mixed with the remaining components such that the particle size of the silicone component after crutching is at least about 20 microns, preferably at least about 35 microns, most preferably at least about 40 microns. Alternatively, preferably in compositions containing soap, a process of the present invention is claimed wherein the silicone component is mixed with a carrier. The carrier, which is selected to facilitate addition of the silicone to the composition, may be selected from the group consisting of paraffins, alcohols, ethers, polyethylene glycols, nonionic surfactants, anionic surfactants, polymers, low molecular weight solvents, and perfume ingredients. Once mixed with the carrier, the silicone/carrier mixture, wherein the silicone component particles have a particle size of at least about 20 microns, preferably at least about 35 microns, most preferably at least about 40 microns, is added to the amalgamator, preferably in the form of flakes.

DETAILED DESCRIPTION OF THE INVENTION

The invention relates to a mild skin cleansing composition in the form of a bar which exhibits superior skin feel, skin conditioning, rinsing benefits and excellent lather performance. This composition also generally provides superior moisturization, as well as less skin irritation, less skin dryness and facial tautness than commercially available toilet soap bars, synthetic toilet bars or other known surfactant based specialty skin cleansing products containing conventional mildness aids and moisturizers. The compositions of the present invention require a specifically defined blend of silicone gum and silicone fluid, and preferably may also contain a cleaning component, skin feel polymers, and conventional cleansing bar components. Bars of the present invention may be in any conventional form, for example aerated, framed, milled, transparent, or antibacterial.

The percentages, ratios and parts herein are given on a weight basis unless otherwise specified.

The essential and optional components of the present invention are set forth below.

The Silicone Component

An essential component of the present compositions is a silicone blend which consists of a silicone gum and a silicone fluid wherein the ratio of gum to fluid is from about 10:1 to about 1:10, preferably from about 4:1 to about 1:4, more preferably from about 7:3 to about 3:7, and most preferably from about 3:2 to about 2:3. The silicone component is present in the composition at a level which is effective to deliver a skin mildness benefit, for example, from about 0.5% to bout 20%, preferably from about 1.5% to about 16%, and most preferably from about 3% to about 12% of the composition. Silicone fluid, as used herein, denotes a silicone with viscosities ranging from about 5 to about 600,000 centistokes, most preferably from about 350 to about 100,000 centistokes, at 25° C. Silicone gum, as used herein, denotes a silicone with a mass molecular weight of from about 200,000 to about 1,000,000 and with a viscosity of greater than about 600,000 centistokes. The molecular weight and viscosity of the particular selected siloxanes will determine whether it is a gum or a fluid. The silicone gum and fluid are mixed together and incorporated into the compositions of the present invention. Polyalkyl siloxanes, such as polydimethyl siloxane, are preferred for use in the silicone component.

The silicone materials useful in the present invention are generally non-volatile and may be either a polyalkyl siloxane, a polyaryl siloxane, a polyalkylaryl siloxane, a polysiloxane with amino functional substitutions, or a polyether siloxane copolymer. The siloxanes useful in the present invention may be endcapped with any number of moieties, including, for example, methyl, hydroxyl, ethylene oxide, propylene oxide, amino, and carboxyl. Mixtures of these materials may also be used and are preferred in certain executions. Additionally, volatile silicones may be used as part of the silicone mixture so long as the final mixture is non-volatile.

The silicone component is present in the cleaning composition as particles which are dispersed and insoluble in the composition matrix. This is the meaning of "insoluble" as used herein. The dispersed silicone particles are at least about 20 microns, preferably at least about 35 microns, and most preferably at least about 40 microns in size in the product. Particle size of the silicone component may be measured in samples of a synthetic surfactant/silicone component premix, a silicone component/carrier mix or of the materials after crutching, as described in the processing description. A thin sample of the silicone/surfactant or silicone/carrier mix is prepared by placing a small quantity (e.g., about 10–50 milligrams) of the sample on a clean microscope slide and dispersing by applying pressure t the cover slip. The sample is then placed in the microscope hot-stage and heated to a temperature (e.g., about 65° C.) at which the silicone/surfactant or silicone/carrier mix undergoes a phase transition into an isotropic phase. This allows the ready identification of silicone particles and determination of their size. Air bubbles are commonly entrapped, but are easily identified by their large dark boundaries. If nonspherical particles are observed, the sample is eliminated. The nonspherical particles are aberrations created during the sample preparation (e.g., by the smearing of particles, or applying too much pressure). the objectives utilized produce a magnification of 209X as determined through the measure of a visual micrometer. Three or four different slides of each sample are prepared with particle size analysis achieved via visual particle counting.

The polyalkyl siloxanes that may be used herein include, for example, polydimethyl siloxanes with viscosities ranging from about 5 to about 600,000 centistokes at 25° C. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, Jul. 20, 1970. Preferably the viscosity ranges from about 50 centistokes to about 100,000 centistokes and most preferably from about 350 centistokes t about 100,000 centistokes.

The polyalkylaryl siloxanes that may be used include, for example, polymethylphenylsiloxanes having viscosities of from about 15 to about 65 centistokes at 25° C. These siloxanes are available, for example, from the General Electric Company as SF 1075 methyl phenyl fluid or from Dow Corning as 556 Cosmetic Grade Fluid. Additionally, poly(dimethyl siloxane) (diphenyl siloxane) copolymers having a viscosity in the range of from about 10 to about 100,000 centistokes at 25° C. are useful. The polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

References disclosing suitable silicones include U.S. Pat. No. 2,826,551, issued Mar. 11, 1958, Geen; U.S. Pat. No. 3,964,500, issued Jun. 22, 1967, Drakoff; U.S. Pat. No. 4,364,837, issued Dec. 21, 1982, Pader; and British Patent 849,433, Woolston, published Sep. 28, 1960. All of these patents are incorporated herein by reference. Also incorporated herein by reference is Silicon Compounds, distributed by Petrarch Systems, Inc., 1984. This reference provides a very good listing of suitable silicone material.

Silicone gums are described by Petrarch and others including U.S. Pat. No. 4,152,416, May 1, 1979, Spitzer et al., and Noll, Walter, Chemistry and Technology of Silicones, New York: Academic Press, 1968. Also describing useful silicone gums are General Electric Silicone Rubber Product Data Sheets SE30, SE 33, SE 54 and SE 76. All of these described references are incorporated herein by reference. "Silicone gum" materials denote high molecular weight polydiorganosiloxanes generally having a mass molecular weight of from about 200,000 to about 1,000,000, preferably from about 400,000 to about 1,000,000. Specific examples include polydimethylsiloxane, (polydimethylsiloxane)(methylvinylsiloxane) copolymer, poly(dimethylsiloxane) (diphenylsiloxane) (methylvinylsiloxane) copolymer, the above siloxanes containing any of the following functional groups:

$$-CH_2CH_2CH_2NH_2;$$
$$-(CH_2)_3NHCH_2CH_2NH_2;$$
$$-(CH_2)_3NH(CH_2)_3NH_2;$$
$$-(CH_2)_3NH(CH_2CH_2CH_2)_xH, \quad x = 2-4;$$

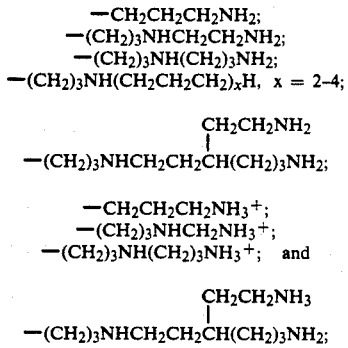

$$-CH_2CH_2CH_2NH_3{}^+;$$
$$-(CH_2)_3NHCH_2NH_3{}^+;$$
$$-(CH_2)_3NH(CH_2)_3NH_3{}^+; \quad \text{and}$$

$$\underset{|}{\overset{CH_2CH_2NH_3}{-(CH_2)_3NHCH_2CH_2CH(CH_2)_3NH_2}};$$

and mixtures thereof. The most preferred silicone gums for use in these compositions are polydimethylsiloxanes preferably having mass molecular weights of from about 400,000 to about 600,000. The gums may contain some minor amount (e.g., 6% to 14% of the total gum weight) of a cyclic volatile silicone.

The Cleaning Component

The mild skin cleansing composition of the present invention may comprise from about 12% to about 90%, preferably from about 20% to bout 85%, of a cleaning component selected from the group consisting of synthetic surfactants, soaps, and mixtures of soaps and synthetic surfactants. Compositions of the present invention may contain from about 0% to about 90%, preferably from about 5% to about 40%, soap in the finished bar. Soap bars, i.e., bars wherein more than 50% of the finished bar is soap, are acceptable but not preferred embodiments of the present invention. Compositions of the present invention may contain from bout 0% to about 90%, preferably from about 12% to about 85%, most preferably from about 12% to about 65%, of a synthetic surfactant or mixtures thereof in the finished bar.

A preferred embodiment of the present invention includes a cleaning component comprising a mild synthetic surfactant or mixtures thereof. A particularly preferred embodiment of the present invention comprises a mixture of a mild synthetic surfactant(s) and soap wherein the final composition contains form about 12% to about 85%, preferably form about 30% to about 65%, of a mild synthetic surfactant(s) and from about 5% to about 40%, preferably from about 5% to about 20% soap. The term "mild synthetic surfactant, as used herein, encompasses surfactants having a value of from about 7 to about 75, preferably from about 7 to about 50, and more preferably from about 7 to about 40, as determined by the skin barrier destruction test described by T. J. Franz in the J. Invest. Dermatol., 1975, 64, pp 190–195, and in U.S. Pat. No. 4,673,525, Small et al., issued Jun. 16, 1987, both incorporated herein by reference.

Preferred mild anionic and amphoteric surfactants used in this invention include suitable alkyl glyceryl ether sulfonates (AGS), acyl sarcosinates, essentially saturated $C_{15}$-$C_{20}$ alkyl sulfates, methyl acyl taurates, N-acyl glutamates, alkyl glucosides, amido-monoethanolamine sulfosuccinates, alkyl monoglyceryl sulfates, acyl isethionates, alkyl sulfosuccinates, alkyl phosphate esters, ethoxylated alkyl phosphate esters, trideceth sulfates, methyl glucose esters, protein condensates, mixtures of ethoxylated alkyl sulfates and alkyl amine oxides, betaines, sultaines, and mixtures thereof. Included in this group of surfactants are the alkyl ether sulfates with 1 to 12 ethoxy groups, especially ammonium and sodium lauryl ether sulfates. Alkyl chains for these surfactants are $C_8$-$C_{22}$, preferably $C_{10}$-$C_{12}$. Also included in the surfactants are the $C_{16}$-$C_{18}$ alkyl sulfates. Preferably acyl isethionate surfactants are $C_{16}$-$C_{18}$, $C_{10}$-$C_{12}$ and $C_{12}$-$C_{14}$. Preferred betaine surfactants include alkyl betaines and amidopropyl betaines. Sultaine surfactants include amidopropyl sultaines. The counterions of the anionic surfactants may be, for example, sodium-, potassium-, ammonium-, trimethyl-, or triethanolamine.

A preferred mild surfactant is sodium coconut alkyl glyceryl ether sulfonate (Coco AGS) which is mild and relatively nonirritating to the skin. This has been demonstrated in in vitro nonclinical mildness testing. While desirable to incorporate into a skin cleanser for its mildness properties, this coco AGS along does not provide optimum lather creaminess. A sodium 90/10 coconut/tallow alkyl AGS distribution is preferred for creaminess. Salts other than the sodium salt, such as triethanolamine-, ammonium- and potassium-AGS, and chain length distributions other than 90/10 coconut/tallow are usable at moderate levels. Also, some soap is preferably added to improve lather volume and speed of lathering.

Certain co-surfactants used in combination with alkyl glyceryl ether sulfonates (AGS) may also provide a creamier and more stable lather. Preferably, these secondary surfactants will also be intrinsically mild. Preferred mild co-surfactants are sodium lauroyl sarcosinates, ethoxylated alkyl sulfates, alkyl sulfosuccinates, amido monoethanolamine sulfosuccinates, sodium cocoylmonoglyceryl sulfates, alkyl monoglyceryl sulfates, sodium cocoyl isethionates, and mixtures thereof. One secondary surfactant that has been found to be especially desirable is sodium lauroyl sarcosinate (trade name Hamposyl L, made by Hampshire Chemical). A preferred cleaning component of the present invention comprises from about 4% to about 50%, preferably from about 8% to about 50%, and most preferably from about 8% to about 30% alkyl glyceryl ether sulfonate and from about 0% to about 50%, preferably from about 1% to about 50%, and most preferably from about 5% to about 20%, of a mild co-surfactant selected from the group consisting of sodium lauroyl sarcosinates, ethoxylated alkyl sulfates, sulfosuccinates, $C_{16}$-$C_{18}$ alkyl sulfates, sodium cocoylmonoglyceryl sulfates, sodium cocoyl isethionates, alkylmonoglycerol sulfates, and mixtures thereof.

$C_{15}$-$C_{20}$ alkyl sulfates surfactants are useful in the present compositions. A preferred alkyl sulfate has a ratio of $C_{16}$-$C_{18}$ in the range of from about 100% $C_{16}$ to bout 100% $C_{18}$ by weight. Sodium cetearyl sulfate, a $C_{16}$-$C_{18}$ alkyl sulfate surfactant, is a mild synthetic surfactant useful in compositions of the present invention. A commercially available $C_{16}$-$C_{18}$ alkyl sulfate is SIPON® EC-111 (formerly SIPEX® EC-111), sodium cetearyl sulfate, which contains approximately 60% $C_{16}$ and 36% $C_{18}$. SIPON® EC-111 is sold by Alcolac Company, Baltimore, Md. 21226. Sodium cetearyl sulfate is a useful co-surfactant with AGS. A preferred embodiment of the present invention comprises a mixture of mild synthetic surfactants wherein the cleansing bar composition contains from about 8% to about 30% AGS, from about 0% to about 15% sodium lauroyl sarcosinate, and from about 20% to about 45% cetearyl sulfate.

Amphoteric betaines and sultaines may be used as sole surfactants, but are more preferred as co-surfactants. Nonionic surfactants cannot be used as the sole surfactant in this product because of their low foaming ability; however, they may be incorporated as co-surfactants.

A particularly preferred cleaning component of the present invention is a mixture of mild synthetic surfactants and soap wherein the ratio of mil synthetic surfactants to soap is form about 0.3:1 to about 14:1, preferably from about 0.75:1 to about 13:1, most preferably from about 1.5:1 to about 13:1. A particularly preferred mixture of mild synthetic surfactants is an alkyl glyceryl ether sulfonate (AGS) acyl sarcosinate/cetearyl sulfate mixture wherein the ratio of AGS to acyl sarcosinate is from about 0.1:1 to about 5.0:1, preferably from about 0.3:1 to about 4.6:1; the ratio of acyl sarcosinate to cetearyl sulfate is from about 0.1:1 to about 0.6:1, preferably from about 0.2:1 to about 0.6:1; and the ratio of alkyl glyceryl ether sulfonate to cetearyl sulfate is from about 0.1:1 to about 1.3:1, preferably from about 0.1:1 to about 0.7:1.

If soap is include din the present compositions it may comprise from about 0% to about 90%, preferably from about 5% to about 40%, most preferably from about 5% to about 20%, alkali metal soap (anhydrous basis) and is an alkali metal soap or mixture of soaps of fatty acids containing from about 8 to about 24, preferably from about 12 to about 20, carbon atoms. Potassium alkali metal soaps may be used, but are not preferred. Sodium alkali metal soaps are preferred in compositions of the present invention. The fatty acids used in making the soaps can be obtained from natural sources such as, for instance, plant or animal-derived glycerides (e.g., palm oil, coconut oil, babassum oil, soybean oil, castor oil, whale oil, fish oil, tallow, grease, or mixtures thereof). The fatty acids can also be synthetically prepared (e.g., by oxidation of petroleum stocks by the Fischer-Tropsch process).

Alkali metal soaps may be made by direct saponification of the fats and oils or by the neutralization of the free fatty acids which are prepared in a separate manufacturing process. Particularly useful are the sodium and potassium salts of the mixtures of fatty acids derived from coconut oil and tallow, i.e., sodium and potassium tallow and coconut soaps. The alkali metal soaps may also be made in situ via adding a base, e.g., NaOH, to convert free fatty acids in the composition mix.

The term "tallow" is used herein in connection with fatty acid mixtures which typically have an approximate carbon chain length distribution of 2.5% $C_{14}$, 29% $C_{16}$, 23% $C_{18}$, 2% palmitoleic, 41.5% oleic and 3% linoleic. (The first three fatty acids listed are saturated.) Other mixtures with similar distribution, such as the fatty acids derived from various animal tallows and lard, ar also included within the term tallow. The tallow can also be hardened (i.e., hydrogenated) to convert part or all of the unsaturated fatty acid moieties to saturated fatty acid moieties.

When the terms ∓coconut oil" and "coconut fatty acid" (CNFA), also defined "coco" and "cocoyl", are used herein, they refer to fatty acid mixtures which typically have an approximate carbon chain length distribution of about 8% $C_7$, 7% $C_{10}$, 48% $C_{12}$, 17% $C_{14}$, 9% $C_{16}$, 2% $C_{18}$, 7% oleic, and 2% linoleic. (The first six fatty acids listed are saturated.) Other sources having similar carbon chain length distribution, such as palm kernel oil and babassu kernel oil, are included with the terms coconut oil and coconut fatty acid.

In the compositions of the present invention, the soap component is preferably sodium soap. Also, it is preferably in such bars that the total soap component comprises (a) from about 20% to about 50% by weight of the soap component of a mixture containing soaps having from 8 to 14 carbon atoms and (b) from about 20% to about 80% by weight of the soap component of soaps having from about 16 to about 20 carbon atoms.

Soaps having such preferred chain length distribution characteristics can be realized by utilizing mixtures of tallow and coconut fatty acids in tallow/coconut weight ratios varying between about 90:10 and bout 50:50. A mixture f soaps of tallow and coconut fatty acids in the tallow/coconut weight ratio of about 80:20 is especially preferred.

Insoluble alkaline earth metal soaps, such as calcium stearate and magnesium stearate, can also be incorporated into compositions of the present invention at levels up to bout 30% of the cleaning component. These materials are particularly useful in toilet bars in which synthetic detergents are present in that they tend to reduce the relatively high solubility which such bars normally have. These alkaline earth metal soaps are not included within the term "soap" as otherwise used in this specification. The term "soap" as used herein refers to the alkali metal soaps.

Polymeric Skin Feel and Mildness Aids

Although not necessary, the presence of at least one other (in addition to the silicone component), preferably polymeric, skin feel and mildness aid is highly desirable in the compositions of the present invention. The polymeric skin feel and mildness aids useful herein have molecular weights of from about 1,000 to about 4,000,000, preferably from about 2,000 to about 3,800,000, and more preferably from about 2,500 to about 3,000,000. These components are generally present at from about 0.01% to about 10%, preferably from about 0.5% to about 5.0% of the skin cleansing bar. Polymeric skin feel and mildness aids may be selected from cationic, anionic, amphoteric, and the nonionic polymers suitable for contact with human skin which provide desirable skin feel benefits. The use of polymeric skin feel and mildness aids in compositions of the present invention may enhance the deposition of the silicone component upon the skin. A preferred skin feel and mildness aid for use in the present compositions is the quaternary ammonium salt of hydroxyethylcellulose JR-400 (made by Union Carbide Corporation), used at levels of from about 0.01% to about 105, preferably from about 0.5% to about 5.0% of the composition.

Polymeric skin feel and mildness aids may be selected for their skin feel, mildness, rinsing or creamy lather benefits. Two or more polymeric skin feel and mildness aids may be combined to enhance synergistically their respective mildness and ease of rinsing benefits for an overall improved bar. Some preferred polymeric aids selected for their mildness benefits are quaternary ammonium salts of hydroxyethylcellulose, guar hydroxy propyltrimonium chlorides, hydroxypropyl guars, and diallyldimonium chloride/ hydroxyethylcellulose copolymers. Other polymers include: copolymers of vinylimidazolium and vinylpyrrolidone, polymeric fluoroethers known as famblins, derivatives of chitosan (including chitosan PCA) and chitin. Some preferred polymeric aids selected for their ease of rinsing benefits are polymeric quaternary ammonium salts of acylamide and dimethylediallyammonium chloride monomers, poly(dimethyl, diallylammonium chloride), and diethyldiallylammonium chloride monomers.

Polymeric skin feel and mildness aids useful herein include quaternary ammonium salts of hydroxyethylcellulose; guar hydroxypropyltrimonium chloride; hydroxypropyl guar, and diallyldimonium chloride/hydroxyethylcellulose copolymer; polymeric quaternary ammonium salts of acylamide and dimethyldiallyl ammonium chloride monomers; poly (dimethyldiallyl ammonium chloride); polymers having the following structural formula:

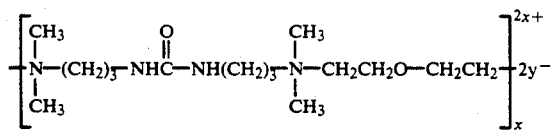

y being a compatible anion, preferably Cl$^-$; cationic and nonionic polysaccharides; cationic and nonionic homopolymers and copolymers derived from acrylic and/or methacrylic acid; cationic copolymers of dimethyldiallylammonium chloride and acrylic acid; cationic homopolyers of dimethyldiallylammonium chloride; cationic polyalkylene, ethoxypolyalkylene imines, copolymers of vinylimidazolium and vinylpyrrolidone, and mixtures thereof.

Some examples of high molecular weight polymeric skin feel and skin mildness aids are: nonionic guar gums; Merquats 100 and 550, made by Merck & Co., Inc.; Jaguar C14S, Jaguar C15 and Jaguar C17 made by Stein Hall; Mirapol A15 made by Miranol Chemical Company, Inc.; and Galactasol 811, made by Henkel, Inc.

The nonionic polymers found to be useful herein include nonionic polysaccharides, e.g., nonionic hydroxypropyl guar gums, offered by Celanese ate Soluble Polymers a Division of Celanese Corp. Another nonionic polymer found to be particularly useful herein is non-derivatized guar gum. A preferred nonionic hydroxypropyl guar gum material is JAGUAR ® HP-60 having molar substitution of about 0.6. Another class of useful nonionics is the cellulosic nonionic polymer class, e.g., HEC and CMC. Other classes of polymers are the polymeric fluoroethers and chitosan and chitin.

Some preferred polymeric skin feel and mildness aids are:
1. JR400 and any higher or lower molecular weight versions. Name: quaternary ammonium salt of hydroxyethylcellulose.
2. Jaguar C15, C14S, C13, C17 and any higher or lower molecular weight versions. Name: Guar hydroxypropyltrimonium chloride.
3. Jaguar HP60 and any higher or lower molecular weight versions. Name: Hydroxypropyl guar.
4. Celquat H60,L200 and any higher or lower molecular weights. Name: Diallyldimonium chloride/hydroxyethylcellulose copolymer.
5. Merquat 550 and any higher or lower molecular weight versions. Name: Polymeric quaternary ammonium salts of acylamide and dimethylediallyl ammonium chloride monomers.
6. Merquat 100 and any higher or lower molecular weight versions. Name: Poly (dimethyldiallyl ammonium chloride).
7. Merquat S and any higher or lower molecular weight versions. Name: polymeric quatenary ammonium salt of acylamide and dimethyldiallyl ammonium chloride and diethyldiallyl ammonium chloride monomers.
8. Mirapol A-15

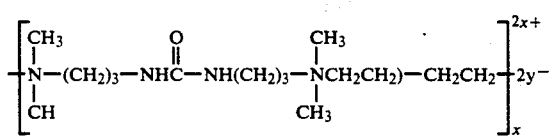

y being a compatible anion, preferably Cl$^-$.

Other suitable cationic polymers are copolymers of dimethylaminoethylmethacrylate and acrylamide and copolymers if dimethyldiallylammonium chloride and acrylamide in which the ratio of the cationic to neutral monomer units has been selected to give a copolymer having a cationic charge. Yet other suitable type of cationic polymers are the cationic starches, e.g., Sta-Lock ® 300 and 400, made by Staley, Inc.

A more complete list of cationic polymers useful in the present invention is described in U.S. Pat. No. 4,438,095, Grollier et al., issued Mar. 20, 1984, incorporated herein by reference. Some of the more preferred cationics are listed in Col. 3, section 2; Col. 5, section 8; Col. 8, section 10; and Col. 9, lines 10–15 of the Grollier et al. patent.

Additional Components

The toilet bar compositions of the present invention may contain additional components conventionally found in toilet bars. Conventional antibacterial agents may be included in the present compositions at levels of from about 0.5% to about 4%. Typical antibacterial agents which are suitable for use herein are 3,4-di and 3,4′,5-tribromosalicylanildes; 4,4′-dichloro-3-(trifluoromethyl)carbanilide; 3,4,4'-trichlorocarbanilide; and mixtures of these materials.

In the compositions of the present invention which contain $C_{15}$–$C_{20}$ alkyl sulfate surfactants, it is highly desirable for the compositions to also include from about 105 to about 50%, preferably from about 15% to about 40%, plasticizer wherein the plasticizer has a melting point of from about 23° C. to about 110° C. The plasticizer can be chosen from a group including, for example, paraffin, fatty acids, fatty alcohols, ethoxylated fatty alcohols, polyethylene glycols and nonionic surfactants (e.g., tallow alcohol ethoxylates TAE80, TAE8, etc.). A preferred plasticizer is polyethylene glycol-150 (PEG-150) which is a polymer of ethylene oxide that conforms generally to the formula $H(OCH_2CH_2)_nOH$ where n has an average value of 150 and has an average mass molecular weight of from about 7,000 to 9,000. PEG-150 is commercially available from Union Carbide as Carbowax 8000. Other plasticizers (binders) are identified in J. Amer. Oil Chem. Soc. 1982, 59, 441. A preferred embodiment of the present invention comprises from about 0.5% to about 16% of a polydimethyl siloxane silicone gum and fluid blend, from about 20% to about 45% $C_{16}$–$C_{18}$ alkyl sulfate surfactant, from about 15% to about 40% plasticizer, from about 5% to about 15% sodium soap, and from about 8% to about 40% mild co-surfactant selected from the group consisting of sodium glycerylether sulfonate, sodium lauroyl sarcosinate, sodium cocoyl isethionate, sodium cocoylmonoglyceryl sulfate, sodium laureth-3 sulfate $(CH_3(CH_2)_{10}CH_2(OCH_2CH_2)_nOSO_3Na$, wherein n has an average value of 3) and mixtures thereof.

Conventional moisturizers/emollients may be included in the present compositions to provide additional skin conditioning benefits and to improve the mildness of the product. The term "moisturizer" is used such that it is synonymous with emollient, and is then meant to describe a material which imparts a smooth and soft feeling to the skin surface.

The moisturizers useful in the present invention are used at a level of from about 0% to about 40%, preferably from about 1% to about 25%, most preferably from about 2% to about 18%, by weight of the composition. Preferred moisturizers are the coco and tallow fatty acids. Some other preferred moisturizers are the nonocclusive liquid water-soluble polyols and the essential amino acid compounds found naturally in the skin. The most preferred moisturizer is a mixture of stearic and lauric acids having a ratio of from about 2:1 to about 1:1. These moisturizers also aid in providing solid bar integrity. In the composition of this invention the high level of moisturizer with soap can also provide for enhanced lather and mildness.

Some examples of moisturizers are long chain $C_{12}$–$C_{22}$ fatty acids, liquid water-soluble polyols, glycerin, propylene glycol, sorbitol, polyethylene glycol, ethoxylated/propoxylated ethers of methyl glucose (e.g., methyl gluceth-20) and ethoxylated/propoxylated ethers of lanolin alcohol (e.g., Solulan-75). Both occlusive and nonocclusive moisturizers may be used in the present invention.

Examples of nonocclusive moisturizers include hexadecyl, myristyl, isodecyl or isopropyl esters of adipic, lactic, oleic, stearic, isostearic, myristic or linoleic acids, as well as many of their corresponding alcohol esters (e.g., sodium isostearoyl-2-lactylate, sodium capryl lactylate), hydrolyzed protein and other collagen-derived proteins, aloe vera gel and acetamide MEA. Preferred nonocclusive moisturizers are compounds found to be naturally occurring in the stratum corneum of the skin, such as sodium pyrrolidone carboxylic acid, lactic acid, urea, L-proline, guanidine and pyrrolidone.

Some occlusive moisturizers include petrolatum, mineral oil, beeswax, lanolin and oil-soluble lanolin derivatives, saturated and unsaturated fatty alcohols such as behenyl alcohol, squalene and squalene, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil. Other examples of both types of moisturizes are disclosed in "Emollients—A Critical Evaluation," by J. Mausner, Cosmetics & Toiletries, May 1981, incorporated herein by reference.

Materials including for example, mineral oils, paraffin wax, fatty sorbitan esters (see U.S. Pat. No. 3,988,255, Seiden, issued Oct. 26, 1976, incorporated by reference herein), lanolin and lanolin derivatives may be included as skin conditioning agents. A free fatty acid, such as coconut fatty acid, may be added to the compositions of the present invention to improve the volume and quality (creaminess) of the lather produced.

Conventional perfumes, dyes and pigments can also be incorporated into compositions of the invention at levels of up to about 5%. Perfumes are preferably used at levels of from about 0.5% to 3%, and dyes and pigments are preferably used at levels of from about 0.001% to about 0.5%. Colorants and also fillers, such as talc and clay, may also be used. Preservatives, e.g., EDTA, generally at a level of less than about 1% of the composition, may be incorporated in the cleansing products to prevent microbiological growth. A particularly preferred embodiment of the present invention comprises from about 20% to about 85% of the alkyl glyceryl ether sulfonate (AGS)/anionic acyl sarcosinate/cetearyl sulfate mixture, from about 5% to about 15% soap, from about 0.01% to about 10% JR-400, from about 15% to about 40% of a plasticizer selected from the group consisting of paraffins, fatty acid, fatty alcohols, ethoxylated fatty alcohols, polyethylene glycols and nonionic surfactants and mixtures thereof which have melting points of from about 23° C. to about 110° C. an from about 2% to about 10% water.

Process for Making the Mild Skin Cleansing Toilet Bar

The cleansing toilet bars of the present invention may be made by conventional techniques well known in the art. A preferred process for preparing the mild skin cleansing compositions of the present invention comprises the conventional steps of crutching, drying, amalgamating, milling, plodding and stamping. In this preferred process, the silicone component is premixed with at least a portion of the mild synthetic surfactant cleansing component (e.g., from about 5% to about 20% of the cleaning component), preferably an acyl sarcosinate, in the absence of soap. This premix is then added to the remaining components in a crutcher and is mixed such that the particle size of the silicone component after crutching is at least about 20 microns, preferably at least about 35 microns, and most preferably at least about 40 microns.

Alternatively, especially in compositions containing soap, the silicone component may be mixed with a carrier. The carrier is selected to facilitate incorporation of the silicone. The carrier, which is used at a minimum level necessary to facilitate the incorporation of the silicone component, e.g., from about 0.5% to about 30% of the finished composition, may be selected from the group consisting of paraffins, alcohols, ethers, polyethylene glycols, nonionic surfactants, anionic surfactants, polymers, low molecular weight solvents, perfume ingredients, and mixtures thereof. Polyethylene glycols are the most preferred carriers. A preferred polyethylene glycol is PEG-150 which is a polymer of ethylene oxide that conforms generally to the formula $H(OCH_2CH_2)_nOH$ wherein n has an average value of 150. PEG-150 is commercially available from Union Carbide as Carbowax 8000. Once mixed with the carrier, the silicone/carrier mixture, wherein the silicone component particles (as measured in the mixture) are at least about 20 microns, preferably at least about 35 microns, and most preferably at least about 40 microns, is added to the amalgamator. In a preferred embodiment, the carrier/silicone mixture is formed into flakes (e.g., by conventional means) prior to addition to the amalgamator. The carrier can also function as a plasticizer or otherwise in the finished composition.

Clinical Assessment of Ultra Mild Toilet Bar

Clinical test procedures used to evaluate toilet bar formulations for skin mildness are set out in U.S. Pat. No. 4,673,525, Small et al., issued Jun. 16, 1987, and Lukacovic et al., J. Soc. Cos. Chem. 39, 355–366 (November/December 1988).

EXAMPLES

The following non-limiting examples describe the mild skin cleansing toilet bars of the present invention, as well as the method of making and using them. These bars, when used in a conventional manner, provide skin cleansing, as well as a superior skin feel, skin conditioning, rinsing, and lathering benefits.

| Ingredient | Example I | Example II | Example III | Example IV |
|---|---|---|---|---|
| Sodium Glyceryl Ether Sulfonate (AGS) | 14.50 | 8.16 | 48.19 | 49.30 |
| Sodium Lauroyl Sarcosinate | 10.65 | 13.61 | 12.08 | 11.33 |
| Sodium Cetearyl Sulfate | 28.20 | 23.81 | — | 21.30 |
| Stearic Acid | 10.25 | 12.70 | 9.47 | — |
| Lauric Acid | 3.70 | 3.63 | 6.28 | — |
| In Situ Soap[5] | 7.00 | 6.80 | 6.96 | — |
| PEG-150 (Carbowax 8000)[3] | 9.00 | — | — | — |
| Paraffin[4] | — | 9.07 | — | — |
| Sodium Isethionate | — | 8.16 | — | — |
| Silicone A[1] | 10.0 | 8.33 | 8.21 | 10.00 |
| Polymer JR 400 | — | 0.50 | — | — |
| Sodium Chloride | 2.0 | 0.70 | 4.25 | 3.62 |
| Titanium Dioxide | 0.20 | 0.23 | 0.24 | 0.22 |
| Perfume | 1.00 | 1.00 | 1.00 | 1.00 |
| Water and Miscellaneous | Balance to 100 | | | |

| Ingredient | Example V | Example VI | Example VII | Example VIII |
|---|---|---|---|---|
| Sodium Glycerylether Sulfonate (AGS) | 4.16 | 8.16 | 29.83 | 14.85 |
| Sodium Lauroyl Sarcosinate | 13.61 | 13.61 | 7.47 | — |
| Sodium Cocoyl Isethionate | 4.00 | — | — | — |
| Sodium Cetearyl Sulfate | 23.81 | 23.81 | — | — |
| Stearic Acid | 12.70 | 12.70 | 10.62 | — |
| Lauric Acid | 3.63 | 3.63 | 7.11 | — |
| Coconut Fatty Acid | — | — | — | 2.25 |
| In Situ Soap[5] | 6.80 | 6.80 | — | — |
| Sodium Soap | — | — | 19.74 | 42.40 |
| Magnesium Soap | — | — | — | 6.33 |
| PEG-150 (Carbowax 8000)[3] | 9.07 | — | — | 9.07 |
| Paraffin[4] | — | 9.07 | — | — |
| Sodium Isethionate | 8.16 | 8.16 | — | — |
| Silicone A[1] | 8.33 | — | 10.00 | 10.00 |
| Silicone B[2] | — | 8.33 | — | — |
| Polymer JR 400 | 0.50 | 0.50 | 0.90 | — |
| Sodium Chloride | 0.70 | 0.70 | 3.64 | 4.90 |
| Sodium Sulfate | — | — | 0.83 | — |
| Titanium Dioxide | 0.23 | 0.23 | 0.22 | 0.22 |
| Perfume | 1.00 | 1.00 | 1.00 | 1.00 |
| Water and Miscellaneous | Balance to 100 | | | |

| Ingredient | Example IX | Example X | Example XI |
|---|---|---|---|
| Sodium Glycerylether Sulfonate (AGS) | — | — | 7.6 |
| Sodium Lauroyl Sarcosinate | 12.08 | 10.65 | 10.65 |
| Sodium Cocoyl Isethionate | 33.19 | — | — |
| Sodium Cocoylmonoglyceryl Sulfate | — | 14.50 | 6.90 |
| Sodium Laureth-3 Sulfate | 15.00 | — | — |
| Sodium Cetearyl Sulfate | — | 28.20 | 28.20 |
| Stearic Acid | 9.47 | 10.25 | 10.25 |
| Lauric Acid | 6.28 | 3.70 | 3.70 |
| In Situ Soap[5] | 6.96 | 7.00 | 7.00 |
| PEG-150 (Carbowax 8000)[3] | — | 9.00 | 9.00 |
| Silicone A[1] | 8.21 | 9.50 | 9.50 |
| Polymer Jaguar C-15 | — | 0.50 | — |
| Polymer Galactosol-811 | — | — | 0.50 |
| Sodium Chloride | 4.25 | 2.00 | 2.00 |
| Titanium Dioxide | 0.24 | 0.20 | 0.20 |
| Perfume | 1.00 | 1.00 | 1.00 |
| Water and Miscellaneous | Balance to 100 | | |

| Ingredient | Example XII | Example XIII |
|---|---|---|
| Sodium Cocoyl Isethionate | — | 45.00 |
| Stearoyl Isethionate | 31.44 | — |
| Disodium Ricinoleamide MEA Sulfosuccinate | 14.25 | — |
| Sodium Dodecylbenzene Sulfonate | — | 1.90 |
| Stearic Acid | 28.3 | 17.57 |
| Coconut Fatty Acid | — | 2.85 |
| Sodium Soap | — | 13.11 |
| Sodium Isethionate | 8.64 | 5.41 |
| Silicone A[1] | 5.00 | 5.00 |
| Sodium Chloride | 0.33 | 0.45 |
| Titanium Dioxide | 0.19 | 0.38 |
| Perfume | 0.95 | 0.95 |
| Water and Miscellaneous | Balance to 100 | |

[1]Silicone A is a 40/60 gum/fluid blend of polydimethylsiloxane, the fluid having a viscosity of about 350 centistokes and the gum having a mass molecular weight of about 500,000, supplied by General Electric.
[2]Silicone B is a 60% polydimethylsiloxane fluid, 40% polydimethylsiloxane (diphenyl) (methylvinyl siloxane) gum blend.
[3]Polyethylene glycol - 150 is commercially available from Union Carbide as Carbowax 8000.
[4]Melting point = 130° F. to 135° F., and is commercially available from National Wax.
[5]In situ soap forms when sodium hydroxide is added to the crutcher containing stearic acid and lauric acid.

Example I

In order to prepare the mild skin cleansing composition of Example I an analysis of the surfactant paste is needed. To illustrate the process, an alkyl (sodium) glyceryl ether sulfonate (AGS) paste with the following nominal analysis is used.

Cationic Titration for $SO_3 = 48.5\%$
$NaCl = 1.5\%$
Moisture $= 43\%$

After the composition of the AGS paste is determined, the crutcher mix is calculated using the AGS/sarcosinate ratio of 4:1 in the finished formula, 55% moisture in the crutcher mix and about 4.0% NaCl in the final bar.

Premixing

A premix of the silicone in AGS is prepared. Eleven pound of silicone (40/60 blend of gum and fluid supplied by General Electric) is mixed with 30.6 lbs. (13.9 Kg) of AGS in a 50 lb. crutcher. The materials are mixed for about 30 minutes with agitation and recirculation with hot (e.g., 150° F.) water on the jacket.

Crutching

Assuming 200 lbs. (90.8 Kg) crutcher mix and the above AGS analysis.

1. The crutcher tank is jacket heated by adding 200° F. (93° C.) hot water and adjusting steam and water valves.
2. 75.7 lbs. (34.4 Kg) of cetearyl sulfate is added an melted to 130°-150° F. (54-65° C.).
3. The agitator and recirculation pump are turned on.
4. 22.6 lbs. (20.3 Kg) of lauroyl sarcosinate (Hamposyl L-30) is added.
5. 9.8 lbs. (4.45 Kg) of stearic acid is added and maintained at 140° F. (60° C.).
6. 4.85 lbs. (2.2 Kg) of lauric acid is added. 2-3 gal. (7.6-11.4 liters) of hot water (205° F., 96° C.) is needed for good mixing.
7. The crutcher contents are mixed for at least 20 minutes and the crutcher mix temperature is maintained at 130°-140° F. (54-60° C.).
8. 5.6 lbs. (2.5 Kg) Carbowax 8000 is added.
9. The mixture temperature is maintained a 140° C. (60° C.).
10. 0.22 lbs. (63 g) of $TiO_2$ is added.
11. When the crutcher mix temperature is at 140° F. (60° C.), NaOH and NaCl are added. 591 grams of 50% NaOH and 561 g of NaCl are blended and added to the crutcher as a slurry.
12. Add 10 lbs. (4.54 Kg) of hot water (205° F., 96° C.) as needed to reduce the crutcher viscosity to obtain good mixing.
13. The silicone/AGS premix is added.
14. The crutcher mix is agitated for about 20 minutes and the temperature is maintained at about 140°-150° F. (60°-65° C.).

Drying

The crutcher mix is dried and cooled using a combination flash chamber and chill roll. The crutcher mix is first heated to approximately 300° F. (149° C.) by a heat exchanger and then flash dried in a chamber at the top of the chill roll. From the flash chamber, the hot dried mix drops onto the nip of the chill roll and applicator roll. The chill roll/applicator roll nip is preferably set to give a uniformly thin, cool 75°-85° F. (24°-29° C.) flake on the chill roll. Typical moisture of the flakes is 1-10%, preferably from about 2-4.5%. The ways to regulate the moisture, in order of preference, are (1) increasing or decreasing steam pressure on the heat exchanger, (2) increasing or decreasing crutcher mix rate to the heat exchanger, or (3) increasing or decreasing crutcher mix temperature to the heat exchanger.

Amalgamating

The flakes are weighed and mixed in a batch amalgamator to obtain a uniform flake size. Preweighed perfume is added to the flakes and mixed n the amalgamator to obtain the desired finished product perfume level. The perfumed flakes are transferred to the mix hopper and directly to the plodder.

Milling

The 3-roll soap mills are preferably set up with the first roll at about 100° F. (38° C.) and the other 2 rolls at about 90° F. (21° C.). The material is passed through the mills two times to provide ribbons. The ribbons are milled one final time prior to plodding.

Plodding and Stamping

The plodder is set up with the barrel temperature at about 110° F.-120° F. (43°-49° C.) and the nose temperature at about 130°-150° F. (54°-65° C.). The ideal plodder is a dual sage plodder that allows use of a vacuum of about 15-24 in. (381.0-609.6) Hg. The plugs are preferably cut in 5" (12.7 cm) billets and stamped with a cold (surface temperature about 5° F. (−15° c.)) die block and stamp using a die liquor such as alcohol.

Alternate Mode of Silicone Addition

The silicone may also be added directly to the amalgamator. In Example I, Carbowax 8000 may serve as a carrier for the silicone. Carbowax is melted and held preferably at a temperature of 140° F. (60° C.). The silicone is mixed into the Carbowax. Once the mixing is complete, the mixture is immediately cooled to ambient temperatures and flakes containing the silicone are formed by conventional means. These flakes are preferably added to the amalgamator prior to addition of the perfume. Alternatively, the Carbowax/silicone premix may be added directly to the amalgamator.

Examples II-XIII

The method of preparing Examples II-XIII is similar to that for preparing Example I with minor variations. For systems which do not contain cetearyl sulfate and plasticizer, all of the surfactants (except the in situ soap and the sarcosinate) are added to the crutcher prior to the addition of stearic acid. Sarcosinate is added after the stearic acid. For systems containing soap, such as in Example VIII, the silicone is preferably added directly to the amalgamator per the alternative mode of silicone addition using any of the carriers described supra.

Method of Using the Mild Skin Cleansing Toilet Bars

The mild skin cleansing toilet bars of the present invention are used by first wetting the skin, rubbing the mild skin cleansing toilet bar upon the skin, and then rinsing the skin with water. In this process, from about 0.2 to about 10 micrograms per $cm^2$ ($\mu/cm^2$) of the silicone component is deposited onto the skin. The silicone component has a particle size of at least about 20 microns in the mild skin cleansing toilet bar. This deposition of the silicone component provides effective skin conditioning. The silicone component preferably consists of a blend of a silicone gum, which has a mass molecular weight of from about 200,000 to about 1,000,000 and a viscosity of greater than about 600,000 centistokes, and a silicone fluid, which has a viscosity of from about 5 centistokes to about 600,000 centistokes. The gum:fluid ratio is rom about 10:1 to about 1:10.

What is claimed is:

1. A mild skin cleansing composition in the form of a bar comprising from about 0.5% to about 20% o a silicone component which consists of a silicone gum and a silicone fluid, wherein the gum:fluid ratio is from about 10:1 to about 1:10 and said silicone component has a particle size of at least about 20 microns.

2. A mild skin cleansing composition according to claim 1 further comprising from about 12% to about 90% of a cleaning component selected from the group consisting of soaps, synthetic surfactants, and mixtures thereof.

3. A mild skin cleansing composition according to claim 2 wherein said cleaning component is a mixture of soap and synthetic surfactant, the composition containing from about 5% to about 40% soap and from about 12% to about 85% synthetic surfactant.

4. A mild skin cleansing composition according to claim 3 wherein said silicone component is present at from about 1.5% to about 16%.

5. A mild skin cleansing composition according to claim 3 wherein the gum:fluid ratio is from about 4:1 to about 1:4.

6. A mild skin cleansing composition according to claim 3 wherein the gum:fluid ratio is from about 7:3 to about 3:7.

7. A mild skin cleansing composition according to claim 6 wherein the ratio of gum:fluid is about 3:2 to about 2:3.

8. A mild skin cleansing composition according to claim 6 wherein the silicone fluid has a viscosity of from about 5 centistokes to about 600,000 centistokes.

9. A mild skin cleansing composition according to claim 8 wherein the silicone gum has a mass molecular weight of from about 200,000 to about 1,000,000 and a viscosity of greater than 600,000 centistokes.

10. A mild skin cleansing composition according to claim 9 wherein both the silicone gum and silicone fluid are polydimethylsiloxanes.

11. A mild skin cleansing composition according to claim 10 wherein the silicone gum has a molecular weight of about 500,000 the silicone fluid has a viscosity of about 350 centistokes, the gum:fluid ration is about 3:2, and the silicone component is present at about 10%.

12. A mild skin cleansing composition according to claim 3 wherein said synthetic surfactant is selected from the group consisting of:
alkyl glyceryl ether sulfonates (AGS);
acyl sarcosinates;
essentially saturated $C_{15}$–$C_{20}$ alkyl sulfates;
methyl acyl taurates;
N-acyl glutamates;
alkyl glucosides;
acyl isethionates;
alkyl sulfosuccinates;
amido-monoethanolamine sulfosuccinate;
alkyl phosphate esters;
alkyl ether sulfates;
alkylmonoglyceryl sulfates;
ethoxylated alkyl phosphate esters;
methyl glucose esters;
protein condensates;
mixtures of ethoxylated alkyl sulfates and alkyl amine oxides;
betaines;
sultaines; and
mixtures thereof.

13. A mild skin cleansing composition according to claim 12 wherein said synthetic surfactant comprises an alkyl glyceryl ether sulfonate which is present at from about 4% to about 50% of the composition.

14. A mild skin cleansing composition according to claim 13 further comprising from about 1% to about 50% of a mild co-surfactant selected from the group consisting of sodium lauroyl sarcosinate, ethoxylated alkyl sulfates, $C_{16}$–$C_{18}$ alkyl sulfates, sodium cocoyl-monoglyceryl sulfates, sodium cocyl isethionates, alkyl-monoglycerol sulfates, and mixtures thereof.

15. A mild skin cleansing composition according to claim 14 wherein said mils synthetic co-surfactant is present at from about 18% to about 55% and is a saturated $C_{16}$–$C_{18}$ alkyl sulfate surfactant.

16. A mild skin cleansing composition according to claim 15 further comprising from about 10% to about 50% of a plasticizer selected from the group consisting of paraffin waxes, fatty acids, nonionic surfactants, fatty alcohols, polyethylene glycols, and mixtures thereof, wherein said plasticizer has a melting point of from about 23° C. to about 110° C.

17. A mild skin cleansing composition according to claim 12 wherein said mild synthetic surfactant is an alkyl glyceryl ether sulfonate/acyl sarcosinate/cetearyl sulfate mix wherein the ratio of alkyl glyceryl ether sulfonate to acyl sarcosinate is from about 0.1:1 to about 5.0:1, the ratio of acyl sarcosinate to cetearyl sulfate is from about 0.1:1 to about 0.6:1, and the ratio of alkyl glyceryl ether sulfonate to cetearyl sulfate is from about 0.1:1 to about 1.3:1.

18. A mild skin cleansing composition according to claim 17 wherein the ratio of alkyl glyceryl ether sulfonate to acyl sarcosinate is about 0.3:1 to about 4.7:1, the ratio of acyl sarcosinate to cetearyl sulfate is from about 0.2:1 to about 0.6:1, the ratio of alkyl glyceryl ether sulfonate to cetearyl sulfate is from about 0.1:1 to about 0.7:1, and wherein the ratio of the alkyl glyceryl ether sulfonate/acyl sarcosinate/cetearyl sulfate mix to soap is from about 0.3:1 to about 14:1.

19. A mild skin cleansing composition according to claim 12 further comprising from about 0.01% to about 10% of a polymeric skin feel and mildness aid.

20. A mild skin cleansing composition according to claim 19 wherein said polymeric skin feel and mildness aid is selected from the group consisting of quaternary ammonium salts of hydroxyethylcellulose; guar hydroxypropyltrimonium chloride; hydroxypropyl guar, and diallyldimonium chloride/hydroxyethylcellulose copolymer; polymeric quaternary ammonium salts of acylamide and dimethyldiallyl ammonium chloride monomers; poly (dimethyldiallyl ammonium chloride); polymers having the following structural formula:

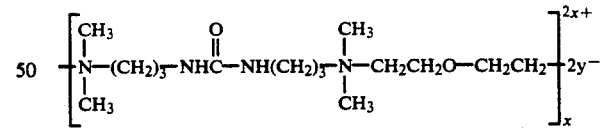

y is a compatible anion, cationic and nonionic polysaccharides; cationic and nonionic homopolymers and copolymers derived from acrylic and/or methacrylic acid; cationic copolymers of dimethyldiallylammonium chloride and acrylic acid; cationic homopolymers of dimethyldiallylammonium chloride; cationic polyalkyleneimines, ethoxypolyalkylene imines, and mixtures thereof.

21. A mild skin cleansing composition according to claim 20 wherein said bar contains a mixture of polymeric skin feel and mildness aids selected from the group consisting of quaternary ammonium salts of hydroxyethylcellulose, polymeric quaternary ammonium salts of acylamide, and dimethyldiallyl ammonium chloride monomers, and mixtures thereof.

22. A mild skin cleansing composition according to claim 20 wherein the polymeric skin feel and mildness aid is a cationic hydroxyethylcellulose.

23. A mild skin cleansing composition according to claim 11 further comprising from about 20% to about 85% alkyl glyceryl ether sulfonate/acyl sarcosinate/cetearyl sulfate mix, from about 5% to about 15% soap, from about 0.01% to about 10% cationic hydroxyethylcellulose, from about 15% to about 40% of a plasticizer selected from the group consisting of paraffins, fatty acid, fatty alcohols, ethoxylated fatty alcohols, polyethylene glycols and nonionic surfactants and mixtures thereof, and from about 2% to about 10% water.

24. A mild skin cleansing composition according to claim 11 further comprising from about 20% to about 45% $C_{16}$-$C_{18}$ alkyl sulfate surfactant, from about 15% to about 40% plasticizer, from about 5% to about 15% sodium soap, and from about 8% to about 40% mild so-surfactant.

25. A mild skin cleansing composition according to claim 24 wherein said mild co-surfactant is selected from the group consisting of sodium glyceryl ether sulfonate, sodium lauroyl sarcosinate, sodium cocoyl isethionate, sodium cocoylmonoglyceryl sulfate, sodium laureth-3 sulfate, alkylmonoglycerol sulfates, ethoxylated alkyl sulfates, and mixtures thereof.

26. In a process for preparing a mild skin cleansing composition according to claim 2 comprising the steps of mixing the components in a crutcher, drying said mixture, amalgamating said mixture, milling said mixture, plodding and stamping said mixture, the improvement wherein said silicone component is premixed with at least a portion of the synthetic surfactant cleaning component in the absence of soap; said premix then being added t the crutcher such that the particle size of the silicone component after crutching is at least about 20 microns.

27. A process for preparing a mild skin cleansing composition according to claim 26 wherein the particle size of the silicone component after crutching is at least about 35 microns.

28. A process for preparing a mild skin cleansing composition according to claim 27 wherein the synthetic surfactant in the premix is an acyl sarcosinate.

29. In a process for preparing a mild skin cleansing composition according to claim 2 comprising the steps of mixing the components in a crutcher, drying said mixture, amalgamating said mixture, milling said mixture, plodding and stamping said mixture, the improvement wherein said silicone component is mixed with a carrier selected from the group consisting of paraffins, alcohols, ethers, polyethylene glycols, nonionic surfactants, anionic surfactants, polymers, low molecular weight solvents, perfume ingredients, and mixtures thereof, the silicone component having a particle size of at lest about 20 microns in said mixture; and said mixture is added to the amalgamator.

30. A process for preparing a mild skin cleansing composition according to claim 29 wherein the silicone/carrier mixture is formed into flakes prior to addition to the agglomerator.

31. A process for preparing a mild skin cleansing bar according to claim 29 wherein the carrier is polyethylene glycol with an average mass molecular weight of from about 7000 to about 9000.

32. A process for enhancing skin conditioning comprising washing said skin in an aqueous system using a toilet bar containing a silicone component with a particle size of at least about 20 microns to deposit from about 0.2 to about 10 micrograms of said silicone component per $cm^2$ of skin.

33. A process for enhancing skin conditioning according to claim 32 wherein the silicone component consists of a blend of a silicone gum and a silicone fluid, and the silicone fluid having a viscosity of from about 5 centistokes to about 600,000 centistokes, and the silicone gum having a mass molecular weight of from about 200,000 to about 1,000,000 and a viscosity of greater than 600,000 centistokes, and wherein the gum:fluid ratio is from about 10:1 to about 1:10.

* * * * *